(12) United States Patent
Weinstein

(10) Patent No.: US 6,293,791 B1
(45) Date of Patent: Sep. 25, 2001

(54) Z-BEND ORTHODONTIC INSTRUMENT AND METHOD

(75) Inventor: Martin Weinstein, Red Bank, NJ (US)

(73) Assignee: Albert Einstein Healthcare Network, Philadelphia, PA (US)

( * ) Notice: Subject to any disclaimer, the term of this patent is extended or adjusted under 35 U.S.C. 154(b) by 0 days.

(21) Appl. No.: 09/521,764

(22) Filed: Mar. 9, 2000

(51) Int. Cl.$^7$ .................................................. A61C 13/14
(52) U.S. Cl. ............................ 433/4; 433/159; 81/424.5; 140/106
(58) Field of Search .................... 433/4, 20, 24, 433/159; 81/424.5, 426; 140/105, 106

(56) References Cited

U.S. PATENT DOCUMENTS

| | | | |
|---|---|---|---|
| 715,674 | * | 12/1902 | Lemon . |
| 1,103,606 | * | 7/1914 | Montag . |
| 1,108,493 | * | 8/1914 | Federspiel . |
| 1,411,823 | | 4/1922 | Weller . |
| 1,531,898 | | 3/1925 | Angle et al. . |
| 1,619,084 | * | 3/1927 | Miller . |
| 2,954,606 | | 10/1960 | Peck . |
| 2,959,858 | * | 11/1960 | Drake . |
| 3,041,729 | * | 7/1962 | Tofflemire . |
| 3,421,553 | * | 1/1969 | Redmon . |
| 3,808,870 | * | 5/1974 | Blancett ........................ 140/106 |
| 4,354,833 | | 10/1982 | Fujita .............................. 433/20 |
| 4,693,246 | * | 9/1987 | Reimels ........................ 81/424.5 |
| 5,084,935 | * | 2/1992 | Kalthoff .............................. 433/4 |
| 5,092,768 | * | 3/1992 | Korn .................................. 433/18 |
| 5,395,236 | * | 3/1995 | Khouri .............................. 433/4 |

OTHER PUBLICATIONS

Dentarum Inc., *Orthodontics*, Catalogue No. 5, Edition 1997, Newtown, Pennsylvania, pp.: Cover & 174–196.

GAC Internataional, Inc., *30 Years Of Putting The Orthondontist First, Orthodontics Products Catalog*, 1997, pp.: Cover, Table of Contents & 140–157, Central Islip, New York.

ORTHO–PLI Corp, *Ortho–Pli, Catalog 1*, pp.: Cover 1–26, Philadelphia, Pennsylvania.

Rocky Mountain Orthodontics 1997, Catalog,, pp.: Cover, XVI and 165–182.

* cited by examiner

*Primary Examiner*—Ralph A. Lewis
(74) *Attorney, Agent, or Firm*—Dann, Dorfman, Herrell and Skillman, P.C.

(57) ABSTRACT

An orthodontic instrument includes a pair of complementary mating die movable together and apart for forming a Z-shaped bend in an orthodontic arch wire. A Z-shaped bend in an orthodontic arch wire is utilized in conjunction with an orthodontic appliance for applying force to a tooth through a bracket thereon to change its inclination and/or rotation respecting the long axis of the tooth, e.g., to upright an angulated tooth or derotate a rotated tooth. Different embodiments of the instrument are utilized in a sideways or an end-on orientation relative to the arch wire to form a Z-bend therein in situ in a patient's mouth, or may operate on the arch wire outside the mouth.

43 Claims, 5 Drawing Sheets

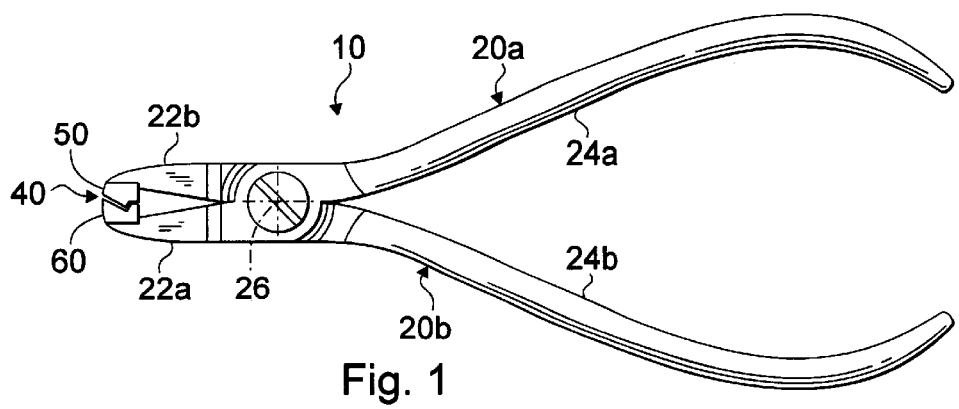
Fig. 1
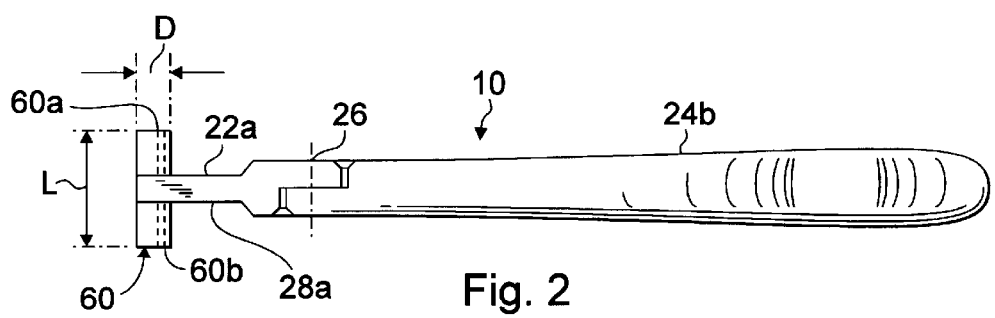
Fig. 2
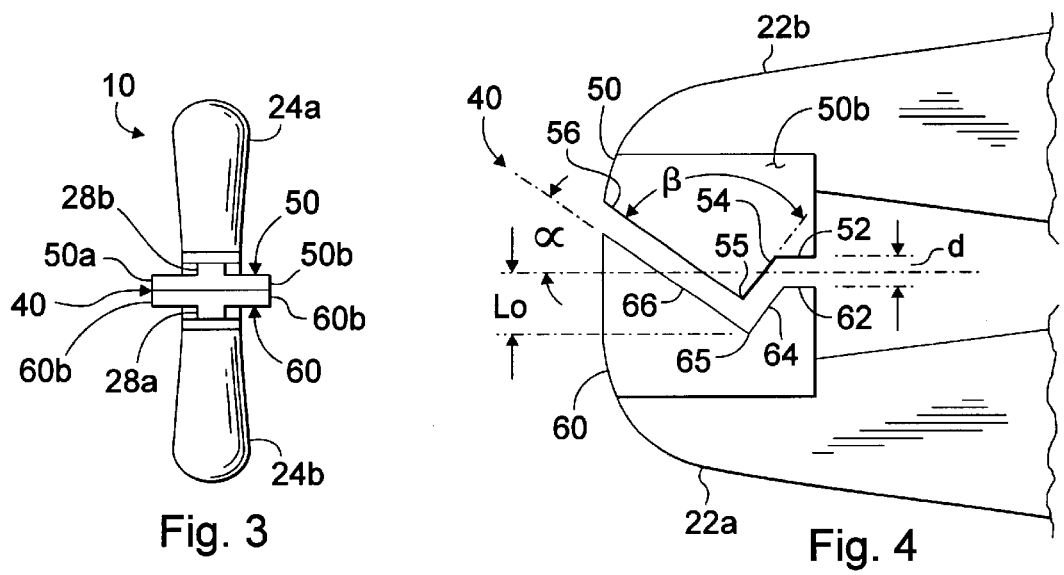
Fig. 3
Fig. 4
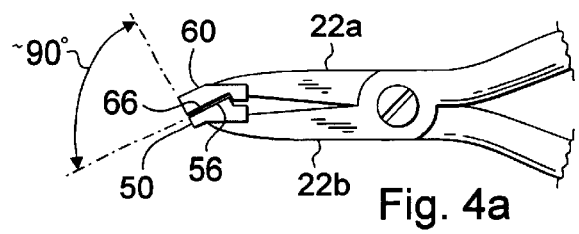
Fig. 4a

Z-BEND ORTHODONTIC INSTRUMENT AND METHOD

The present invention relates to an orthodontic instrument and method, and, in particular, to an orthodontic instrument producing a Z-shaped bend in a wire and to a method of treatment employing a Z-shaped bend in a wire.

Orthodontics includes the installing of an orthodontic appliance, a brace or set of braces, on the teeth of a patient in order to straighten and align crooked and/or misaligned teeth. Following a treatment plan, an orthodontist installs the initial appliance by bonding or banding brackets to the surface of each tooth. Each bracket has a slot referred to as an arch wire slot, made to accept and hold an arch wire, and has a number of tie wings (typically four, but two, three or six are also common) near the arch wire slot. The force exerted between the arch wire and the bracket is transmitted to the tooth via the bracket to move the tooth towards the desired position. The arch wire is typically held in each bracket by a ligating module, i.e. an elastic ligature (a small plastic o-ring) or a thin metal ligature wire, which encircles the tie wings of the bracket, thereby securing the arch wire in the arch wire slot therein. So-called self-ligating brackets and arch wire tubes on molar bands serve a like purpose of engaging the arch wire and a bracket to exert force on a tooth.

Because the long axis of various teeth are at different angles with respect to the occlusal plane, the imaginary planar surface on which upper and lower teeth meet, different brackets are utilized for different teeth, e.g., central, lateral, cuspid, bicuspid, molar and so forth. The differences are manifest as differing angles between the bracket and tooth surface and different spacings therefrom, so as to account for the differing angulation, inclination and extraction needs of the orthodontic correction, so as to exert forces on the tooth to produce lateral movement, translation, rotation, torque, extraction and so forth.

Proper placement of the bracket on a tooth is difficult, particularly where the teeth are seriously misaligned and/or occluded. This is because the configuration of each bracket is determined by the final location and position of each tooth after the orthodontic correction is complete, not as the teeth are when the orthodontist selects and installs the brackets at the commencement of treatment. Moreover, each bracket must be bonded or banded to a tooth in precisely the proper position with respect to that particular tooth in relation to its long axis and its proper position in the mouth. Accordingly, it is difficult and requires great skill to install the brackets in exactly the right position on each tooth. The difficulty is increased where a tooth is misshaped due to an injury, poor restoration or congenital defect. While periodic orthodontic adjustment of the arch wire continues the exertion of corrective force on each tooth, it can not correct for significantly misplaced or misaligned brackets, which can only be corrected by replacement of the bracket or band, or by attempting to manually form the arch wire to include a number of bends to compensate for these discrepancies, each of which is a time-consuming and costly procedure.

Moreover, correction of inclined, angulated and derotated teeth using conventional orthodontic practice relies upon the fixed inclination and rotation, respectively, that are built into the particular bracket selected, for example, a fixed amount of 5° or 7° or 9° of correction in either inclination or rotation, or in both. If a different correction is required, or if a bracket is mis-positioned or mis-aligned, a different bracket or different bracket placement becomes necessary. This is a time-consuming and costly procedure requiring the removal of the bracket from the tooth, cleansing, drying and otherwise preparing the tooth for bonding (or banding) and bonding (or banding) the new bracket in the proper position with the required precision.

While one might attempt to correct tooth inclination and/or rotation by bending the arch wire, as is done conventionally for other corrections, there is no instrument available to make the necessary complex bends, as there are for other simpler, conventional bends such as the offset bends formed by a conventional bayonet (step) bending plier or the wire-shortening V-bend formed by a conventional stop (V bend) plier. Because the bends that are required to correct inclination and rotation must be very precise, they do not lend themselves to conventional arch wire bending practice. Even if one were to attempt to so bend the arch wire, it must be done outside the patient's mouth, thus requiring removal of the arch wire, and so would also be a time-consuming and costly procedure. In addition, a practitioner is unlikely to be able to make bends in the arch wire having the necessary precision and alignment due to the precision and complexity of the necessary bends in the arch wire. Any error in the bending produces undesired forces on the tooth in question as well as on adjacent teeth.

Accordingly, there is a need for an instrument for making a bend in an orthodontic arch wire suitable for correcting rotation and/or inclination of a tooth. It is desirable that the instrument facilitate in situ bending of the arch wire with only the arch wire removed from only a few brackets, at least for certain corrections on certain teeth.

To this end, the instrument of the present invention comprises a pair of complementary mating die for forming at least two portions of a Z-shaped bend in an wire, wherein unbent portions of the wire adjacent the Z-shaped bend are substantially co-linear; and a mechanism adapted to move the complementary mating die apart and to move the complementary mating die together, whereby the arch wire is formed to said Z shape when between said complementary mating die when said die move together.

Further, the method of adjusting an arch wire of an orthodontic appliance of the present invention comprises:
identifying a tooth to be angulated or rotated;
releasing the arch wire from a bracket on the identified tooth and from brackets on at least one tooth distal and one tooth mesial therefrom;
forming a Z-shaped bend in the arch wire using a Z-bend forming instrument, the Z-shaped bend having a longer diagonal portion between two substantially parallel shorter portions;
placing a longer diagonal portion of the Z-shaped bend into the bracket of the identified tooth; and
securing the arch wire in the brackets on the identified tooth and on the at least one tooth distal and one tooth mesial therefrom.

DESCRIPTION OF THE DRAWING

The detailed description of the preferred embodiments of the present invention will be more easily and better understood when read in conjunction with the FIGURES of the Drawing which include:

FIG. 1 is a side view of an exemplary embodiment of an orthodontic instrument in accordance with the present invention;

FIG. 2 is a top view of the orthodontic instrument of FIG. 1;

FIG. 3 is an end view of the orthodontic instrument of FIG. 1;

FIG. 4 is an enlarged side view of an exemplary embodiment of a plier head of the orthodontic instrument of FIG. 1;

FIG. 4A is an enlarged side view of an alternative exemplary embodiment of a plier head of the orthodontic instrument of FIG. 1;

Figure 5:
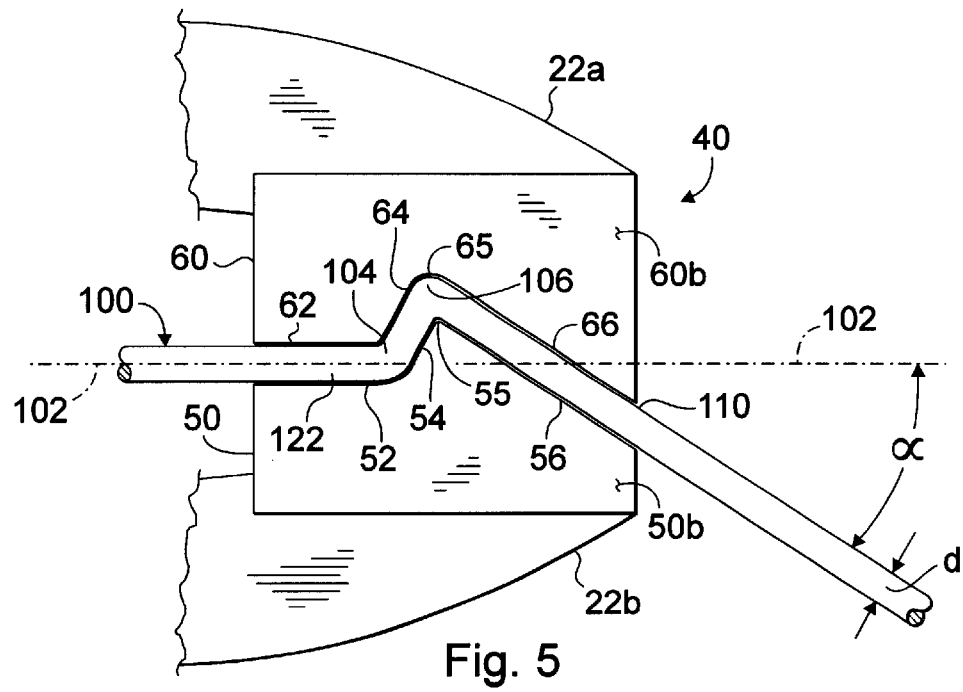
FIGS. 5 and 6 illustrate the method for making a Z-shaped bend using an instrument including the exemplary embodiments of the present invention illustrated in FIGS. 4 and 4A.

In the Drawing, where an element or feature is shown in more than one drawing figure, the same alphanumeric designation may be used to designate such element or feature in each figure, and where a closely related or modified element is shown in a figure, the same alphanumerical designation primed may be used to designate the modified element or feature.

DESCRIPTION OF THE PREFERRED EMBODIMENTS

Owing to the difficulties of correcting inclination and/or rotation of a tooth as described above, the present inventor has discovered that a Z-shaped bend made in an arch wire of an orthodontic appliance can, if made with suitable precision, be utilized to change the inclination and/or rotation of a tooth. Such Z-shaped bend requires substantial symmetry and that the portions of the arch wire on either side of the bend be substantially co-linear, i.e. in substantially the same relative positional relationship as they were prior to the Z-bend being made. Because four bends must be made to form a Z-bend in the arch wire, and because the lengths of each segment of the Z-bend be of particular length and at a particular angle, it is unlikely, if not essentially impossible, that a practitioner could make the required bends with the necessary angles and lengths. Even if one did manage to do so, it could not be done consistently with accuracy as is necessary for satisfactory orthodontic practice or quickly enough as to avoid the use of excessive time and undesirably increasing the cost of treatment. The difficulty of forming such bend is likely increased where a tooth is misshaped due to an injury, poor restoration or congenital defect. Accordingly, the instrument according to the present invention described herein is particularly suited and useful in the method according to the present invention including forming of Z-shaped bends in orthodontic arch wires, when the arch wire is in situ in a patient's mouth or when it is outside the mouth.

In an orthodontic instrument 10 in accordance with the present invention, the instrument is embodied in a mechanism having two jaw portions operably connected for moving respective ones of a pair of complementary mating die together and apart for forming a wire placed between the mating die. Such operable connection may be a pivotal or a sliding connection or other form of connection that allows the complementary mating die to move together and apart. The complementary mating die define at least two of the three portions of a Z-shaped bend made in a wire when the mating die are moved together with the wire therebetween.

FIGS. 1, 2 and 3 are side, top and end views, respectively, of an exemplary embodiment of an orthodontic instrument 10 in accordance with the present invention. Therein, a plier 10 includes two complementary plier halves 20a, 20b pivotally connected at a pivot 26. Each plier half 20a, 20b includes a respective jaw portion 22a, 22b at one end thereof and a respective handle portion 24a, 24b at the other end thereof, with the respective jaw portions juxtaposed and the respective handle portions juxtaposed on opposite sides of the pivot so that moving the handle portions 24a, 24b relatively closer or distant one another likewise moves the jaw portions 22a, 22b relatively closer or distant one another. A plier head or jaw 40 includes a pair of complementary mating die 50, 60 attached respectively to the ends of jaw portions 22b and 22a. Thus, pliers 10 may be utilized to form a workpiece, such as an orthodontic arch wire, placed between complementary mating die 50, 60 when handle portions 24a, 24b are moved closer together to close die 50, 60 on the workpiece.

Plier head 40 extends outwardly in both directions from jaw portions 22a, 22b so as to provide working room on die 50, 60 on either side thereof to facilitate the use of plier 10 to form an arch wire while the arch wire is in situ in the mouth of the patient. Head 40 and die 50, 60 are of length L between their respective opposite ends, 50a, 50b and 60a, 60b, where length L is preferably about 15–17 mm, and are centered to extend symmetrically with respect to jaw portions 22b, 22a. Preferably, jaw portions 22a, 22b are narrowed proximate head 40 as illustrated by the narrowed portions 28a, 28b in FIGS. 2 and 3, for example, so as to make available a greater working length of die 50, 60 without increasing the length L thereof. Head 40 and die 50, 60 are of depth D, where depth D is preferably about 5–7 mm, as is consistent with the size of the bend to be made in the arch wire as described below. The edges and corners of plier head 40 and plier halves 20a, 20b are rounded so as to avoid sharp edges and points that might injure a patient.

The preferred shape of a bend in an arch wire to effect rotation of a tooth is a "Z-shaped" bend wherein the respective portions of the arch wire at the two ends of the Z-bend are in substantially the same relationship as they were before the Z-bend was made, i.e. the portions are substantially co-linear or co-axial. The central portion of the Z-bend, i.e. the generally longer diagonal portion joining opposite ends of the two parallel shorter portions, is at a predetermined angle with respect to the axis of the arch wire and has a predetermined length, and thus passes through the arch wire slot of the bracket at an angle to bear more forcefully on diagonally opposite ends of the arch wire slot so as to exert a torque or rotational force against the bracket to correspondingly rotate the tooth. If the arch wire portions at opposite ends of the Z-bend are not substantially co-linear, then the bend will exert force on the tooth through the bracket bonded thereto to move the tooth other than just in the desired rotation, but in an undesired manner, e.g., such as labially or lingually. To this end, the lengths of the two parallel shorter portions of the "Z" must be of substantially the same length and must each be in substantially the same angular relationship to both the central portion of the Z and to the unbent co-linear sections of the arch wire. It is the desirability of this precise relationship of the bent arch wire that renders the making of a proper Z-bend extremely difficult, if not virtually impossible, with conventional wire bending methods and instruments.

If the Z-bend is made to lie in a plane substantially parallel to the occlusal plane, it will exert a torque on the tooth substantially about the long axis of the tooth, thereby to effect rotation of the tooth about its long axis to correct the rotation of the tooth. If, on the other hand, the Z-bend is made to lie in a plane substantially perpendicular to the occlusal plane, and thus substantially in a plane containing the long axis of the tooth, it will exert a torque on the tooth substantially to rotate the long axis of the tooth, thereby to effect rotation of the long axis of the tooth to correct the inclination of the tooth. Thus, the Z of the "Z-shape" may be in the usual orientation or a mirror-image orientation, or may be rotated ±90°0 from either orientation.

The novel arrangement of the plier in accordance with the present invention facilitates the making of the Z-bend in any orientation, and, in many cases, with the arch wire wholly or at least partly in situ in the mouth of the patient. To this end, FIG. 4 is a side view of an exemplary embodiment of plier head 40, enlarged from the view of FIG. 1, to show the particular shape and arrangement of complementary mating die 50, 60 for forming a Z-shaped bend in two steps. Die 50 is a positive or "male" die in that it has a projecting ridge 55 at the intersection of planar surface 54 which extends upwardly from a base planar surface 52 and of planar surface 56 that extends downwardly from the ridge line 55 and passes through the plane in which planar surface 52 lies (upwardly and downwardly being understood with respect to a particular die as being in a direction away from the bulk of that die or towards the bulk of that die, respectively). Die 60 is a negative or "female" die in that it has a trough with a bottom line 65 at the intersection of planar surface 64 which extends downwardly from a base planar surface 62 and of planar surface 66 that extends upwardly from the bottom line 65 and passes through the plane in which planar surface 62 lies. Planar surfaces 52, 54, 56 and ridge 55 extend the full length L of die 50 and planar surfaces 62, 64, 66 and trough 65 extend the full length L of die 60 so that die 50 and 60 are each of uniform shape over their entire length L. As a result, the bend formed by die 50, 60 at the respective ends 50a, 60a thereof is of opposite hand to the bend formed at the opposite ends 50b, 60b thereof, so that one plier 10 may be utilized to form Z bends to be utilized to provide either positive or negative angular correction of tooth inclination and/or rotation.

Die 50 and 60 are shown spaced apart by a gap of distance "d" which corresponds to the diameter or width of a typical arch wire, i.e. are shown in the position the die are in at the completion of the forming of a wire placed therebetween. Planar surfaces 52, 62 hold the portion of the arch wire that is not bent and that will remain co-linear after the Z-bend is formed. Planar surfaces 54, 64 define the length of the shorter parallel portions of the "Z" and the angle thereof with respect to planar surfaces 52, 62 defines the angle γ to which the arch wire is bent between the shorter portions of the "Z" and the substantially co-linear portions of the arch wire. Planar surfaces 56, 66 define the angle β of the longer central portion of the "Z" with respect to planar surfaces 54, 64 which defines the angle to which the arch wire is bent between the shorter portions of the "Z" and the longer central portion thereof, thereby to define the predetermined angle α between the central portion of the "Z" and the substantially co-linear portions of the arch wire. Preferably, the distance between ridge 55 and the exterior end of die 50 along planar surface 56 and the distance between trough 65 and the exterior end of die 60 along planar surface 66 correspond to the length of the central portion of the "Z", thereby to consistently form Z-bends having a predetermined length of the central portion of the "Z".

FIG. 4A is a modified embodiment of the plier shown in FIG. 4 in which the exterior ends of mating die 50, 60 are angled so as to be at substantially right angles with respect to planar surfaces 56, 66, respectively. As a result, the arch wire will be substantially perpendicular to the ends of die 50, 60 where it exits the die. This arrangement is thought to facilitate the making of the second bend in the arch wire to complete the Z-bend and to obtain Z-bends having consistent length of the central portion of the "Z".

Figure 6:
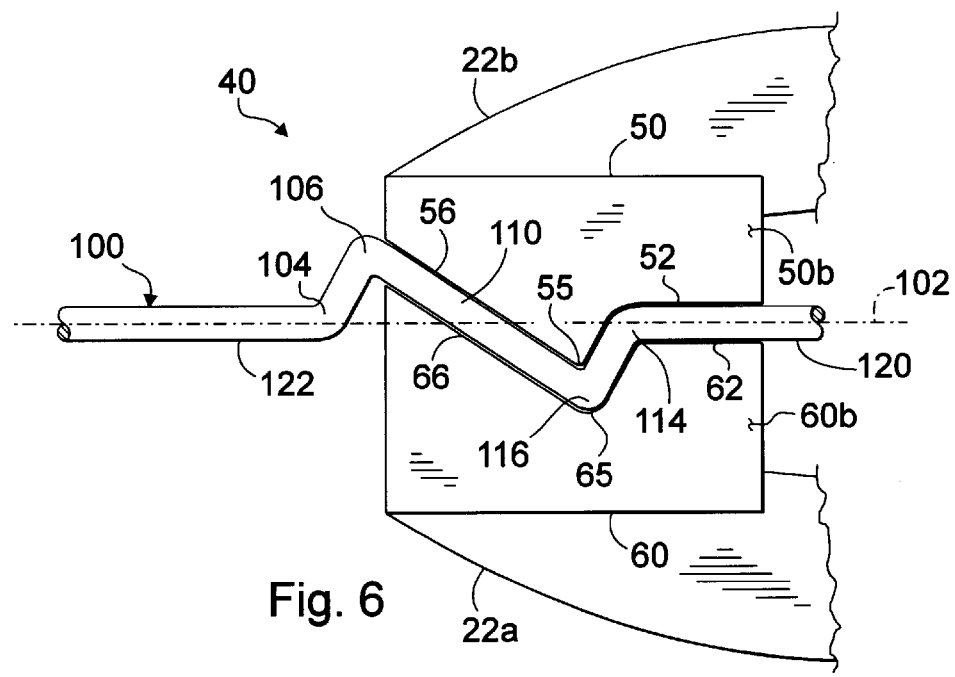
Figure 7:
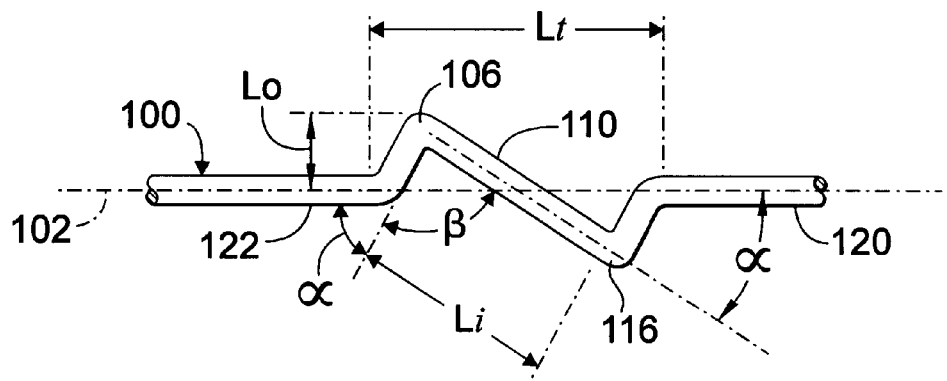
FIG. 7 is a view of a wire having a Z-shaped bend of the sort made in accordance with the present invention, for example, a Z-shaped bend made by the instrument of FIG. 1 used in the manner of FIGS. 5 and 6.

The method of forming a Z-bend in an orthodontic arch wire is described in relation to FIGS. 5 and 6 to produce the arch wire having a Z-shaped bend shown in FIG. 7 using a plier 10 of the type shown in FIGS. 1, 4 and 4A, for example, i.e. a plier forming a Z-bend in two steps. Arch wire 100 having a central axis 102 and a dimension "d" is placed between complementary mating die 50, 60 of orthodontic plier 10 in the desired orientation at one end thereof, for example, at respective ends 50b, 60b thereof as illustrated, and the handles 24a, 24b thereof are squeezed together to move die 50 and 60 together until limited by the dimension "d" of wire 100. As die 50, 60 move together, wire 100 is formed by ridge 55 moving close to trough 65 thereby to form bends 106, 104 in wire 100, i.e. to form one of the short parallel portions of the "Z". Portion 110 of wire 100 extends outwardly from die 50, 60 at the angle α defined by planar surfaces 56, 66 or die 50, 60, respectively, in relation to wire axis 102. Then arch wire 100 is released from plier 10 and plier 10 is rotated 180° about pivot 26, for example, so that the handles 24a, 24b which extended to the left in FIG. 5 now extend to the right. The same end can be reached where the position of plier 10 is not changed and arch wire 100 is turned 180°.

Arch wire 100 is placed between complementary mating die 50, 60 of orthodontic plier 10 in the desired orientation at the same end thereof, for example, at respective ends 50b, 60b thereof as illustrated. Wire 100 is positioned with the portion 110 thereof between planar surfaces 56, 66 and with the short portion of the "Z" between bends 104 and 106 close to or touching the exterior surface of die 60. The handles 24a, 24b of plier 10 are then squeezed together to move die 50 and 60 together until limited by the dimension "d" of wire 100. As die 50, 60 move together, portion 110 of wire 100 is formed by ridge 55 moving close to trough 65 thereby to form bends 116, 114 in wire 100, i.e. to form the other of the short parallel portions of the "Z". Portion 110 of wire 100 is within die 50, 60 at the angle α defined by planar surfaces 56, 66 or die 50, 60, respectively, in relation to wire axis 102, whereas portion 120 of wire 100 extends outwardly from die 50, 60.

Arch wire 100 is then released from plier 10 and has formed therein a symmetric Z-shaped bend wherein the axis of wire 100 in unbent portions 120, 122 thereof are substantially co-linear owing to the fact that substantially identical and symmetrical bends are precisely formed in wire 100 by die 50, 60 of plier 10 in two forming steps. Moreover, the two shorter portions of the Z-bend at the ends of longer diagonal portion 110, i.e. the portions between bends 104 and 106 and between bends 114 and 116, are substantially parallel to each other as a result of such symmetry.

The angle α between the central diagonal portion 110 of the Z-bend and the axis 102 of wire 100 is typically between about 15° and about 25°, and preferably is about 20°. The angles β and γ are not critical although an angle β between about 75° and 95° is satisfactory, and an angle β of about 90° is preferable. The distance Lo which is the distance to bends 106, 116 of the bent arch wire from the co-linear axis 102 of the unbent portions 120, 122 of arch wire 100 is preferably between about 0.75 mm and 1.0 mm. The length Li of central portion 110 is typically about 4–8 mm, and is preferably about 5–6 mm, so as to be of sufficient length to be longer than the width of most brackets which typically have widths between about 3.5 and 4.5 mm. In addition, the total length of the Z bend between the unbent portions 120, 122 of wire 100 should be less than about 8–9 mm, and preferably less than about 7 mm, so that the unbent portions 120, 122 of arch wire 100 can be placed into the brackets bonded to adjacent teeth in the distal and mesial directions of the arch.

In clinical use, the arch wire 100 of an orthodontic appliance is released from the bracket bonded to the tooth that is to be inclined and/or rotated and from the brackets bonded to one or more teeth adjacent thereto in both the distal and mesial directions of the arch by removing the ligating modules therefrom so as to provide a free length of the arch wire 100 in which to form a Z-shaped bend. Typically, arch wire 100 is marked before removal from the bracket to indicate the location of the bracket thereon so that the desired Z-bend can be accurately placed along arch wire 100. After the bend is made, arch wire 100 is repositioned into the brackets and is secured by ligating modules. In certain regions of the mouth, for example the molar regions, it may be advisable to remove the arch wire after marking the location where the Z-bend is to be formed, so as to actually form the Z-bends with the arch wire 100 outside the patient's mouth, particularly when using a plier 10 as in FIGS. 1, 4 and 4A where the Z-bend is formed in two steps.

Figure 8:
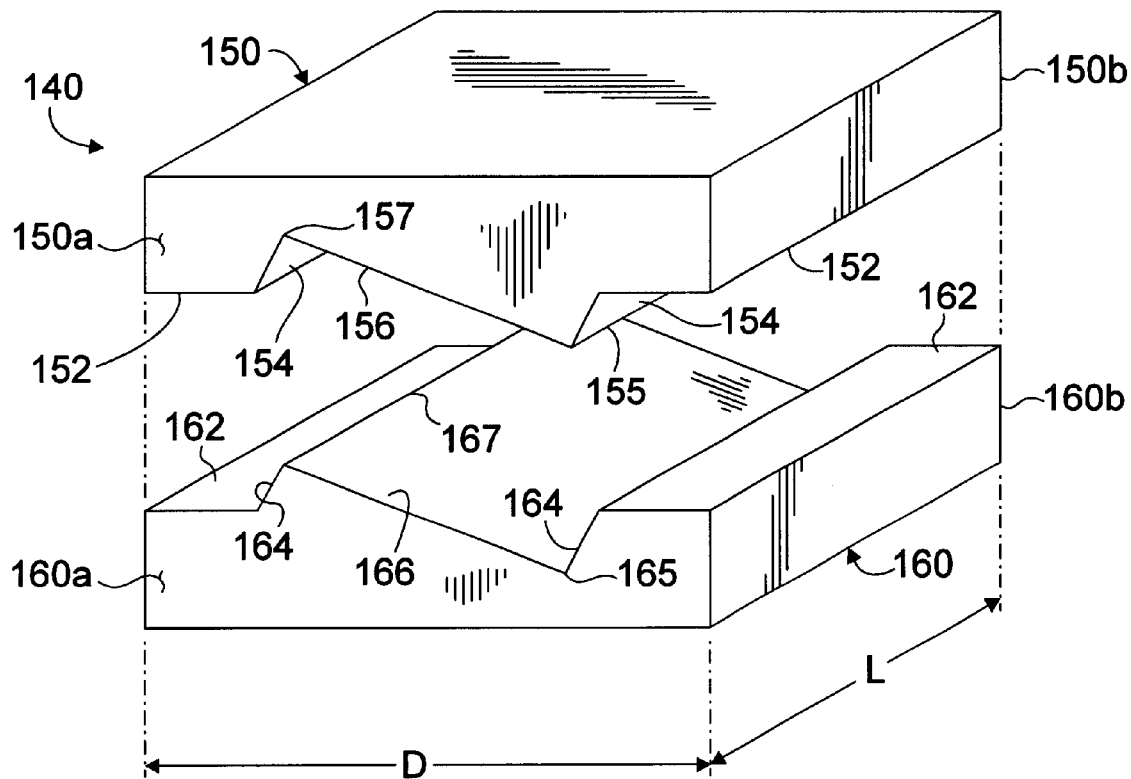
FIG. 8 is a perspective view of another exemplary embodiment of a plier head for an orthodontic instrument in accordance with the present invention.

FIG. 8 is a perspective view of an alternative embodiment of a plier head 140 that forms a complete Z-bend in a single step and which can be employed in plier 10 in place of plier head 40 that forms a Z-bend in two steps. In FIG. 8, complementary mating die 150 and 160 of plier head 140 correspond to complementary mating die 50 and 60 of plier head 40, and the features thereof designated by numerals "1xx" correspond to the features designated by numerals "xx" in FIGS. 4 and 4A. Each of die 150, 160 have a respective angled planar surface 156, 166, respectively, that is angled at the angle α with respect to planar surfaces 152 and 162, respectively, thereby to define the predetermined angle α of the central portion 110 of the Z-bend formed in an arch wire 100 by mating die 150, 160. The two planar surfaces 152 of die 150 are co-planar as are the two planar surfaces 162 of die 160. Angled planar surfaces 154 of die 150 are parallel to each other and define a ridge line 155 and a trough line 157 at their intersections with planar surface 156, thereby to define a symmetrical Z-shaped die 150. Likewise, angled planar surfaces 164 of die 160 are parallel to each other and define a ridge line 165 and a trough line 167 at their intersections with planar surface 166, thereby to define a symmetrical Zshaped die 160 complementary to and mating with Z-shaped die 150.

Planar surfaces 152, 154, 156 and ridge 155 and trough 157 extend the full length L of die 150 and planar surfaces 162, 164, 166 and trough 165 and ridge 167 extend the full length L of die 160 so that die 150 and 160 are each of uniform shape over their entire length L. As a result, the bend formed by die 150, 160 at the respective ends 150a, 160a thereof is of opposite hand to the bend formed at the opposite ends 150b, 160b thereof, so that one plier 10 may be utilized to form Z bends to be utilized to provide either positive or negative angular correction of tooth inclination and/or rotation.

Figure 9A:
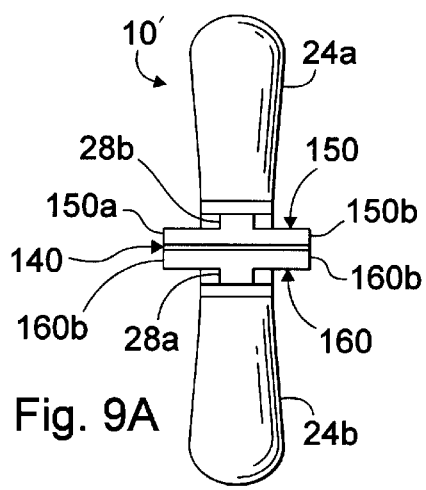
FIGS. 9A and 9B are end and side views, respectively, showing the plier head of FIG. 8 with the orthodontic instrument of FIG. 1.
Figure 9B:
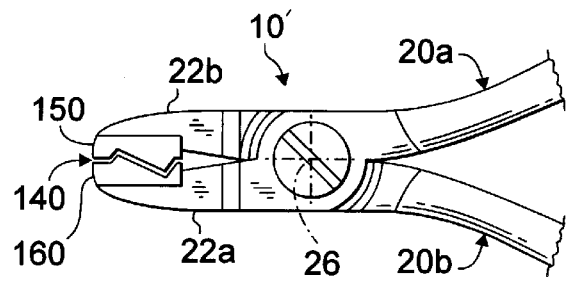

FIGS. 9A and 9B are end and side views, respectively, showing the plier head 140 of FIG. 8 attached to an orthodontic plier 10' that is otherwise like the plier of FIG. 1 as described above. Plier head 140 includes complementary mating die 150, 160 attached to jaw portions 22b, 22a, respectively, of plier 10' with the ridges 155, 167 and troughs 157, 165 thereof lying in a direction transverse to the plier halves 20a, 20b, so as to be utilized in a sideways position, i.e. with the handles 24a, 24b lying in the same general direction generally parallel to the arch wire. 100. Using plier 10' with mating die 150, 160, complete Z-bends as shown in FIG. 7 may be formed in an arch wire in one forming step without the need to rotate the plier 10' (or the arch wire 100) to perform a second forming step as is the case with plier head 40 described above. The bend formed by die 150, 160 at the respective ends 150a, 160a thereof is of opposite hand to the bend formed at the opposite ends 150b, 160b thereof, so that one plier 10' may be utilized to form Z bends to be utilized to provide either positive or negative angular correction of tooth inclination and/or rotation, simply be selecting the appropriate end 150a, 160a or 150b, 160b of die 150, 160 of plier head 140.

Die 150, 160 of plier 10' are typically of a length L of about 15–17 mm and of a depth of about 9–12 mm, and the planar surfaces 152, 154, 156, 162, 164, 166 are of like dimension and at like angles to those described above to form Z-bends having the angles and dimensions described above in relation to FIG. 7, for example.

Figure 10A:
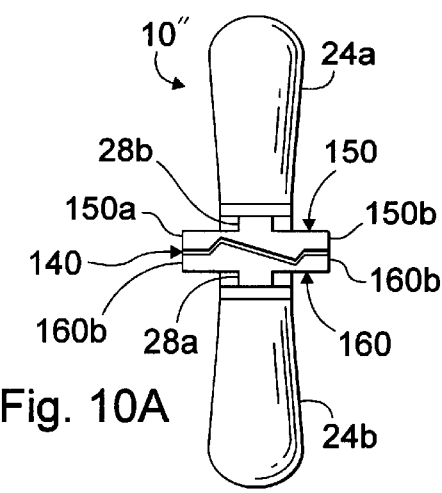
FIGS. 10A and 10B are end and side views, respectively, showing the plier head of FIG. 8 with the orthodontic instrument of FIG. 1, but rotated 90° relative to FIGS. 9A and 9B.
Figure 10B:
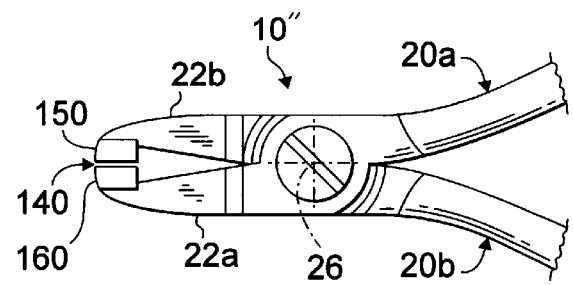

FIGS. 10A and 10B are end and side views, respectively, showing the plier head 140 of FIG. 8 attached to an orthodontic plier 10" that is otherwise like the plier of FIGS. 1 and 9A, 9B as described above, but with the plier head 140 rotated 90° relative to its orientation in FIGS. 9A and 9B. Plier head 140 includes complementary mating die 150, 160 attached to jaw portions 22b, 22a, respectively, of plier 10" with the ridges 155, 167 and troughs 157, 165 thereof lying in the same general direction as the plier halves 20a, 20b, so as to be utilized in an end-on position, i.e. with the handles 24a, 24b substantially perpendicular to the arch wire 100. Using plier 10" with mating die 150, 160, complete Z-bends as shown in FIG. 7 may be formed in an arch wire in one forming step without the need to rotate the plier 10" (or the arch wire 100) to perform a second forming step as is the case with plier head 40 described above.

Die 150, 160 of plier 10" are typically of a length L of about 5–10 mm and of a depth of about 9–12 mm, and the planar surfaces 152, 154, 156, 162, 164, 166 are of like dimension and at like angles to those described above to form Z-bends having the angles and dimensions described above in relation to FIG. 7, for example.

A significant advantage of the end-on arrangement of plier 10' is that it is much easier to place complementary mating die 150, 160 thereof on an arch wire while the arch wire is in situ in the patient's mouth, thereby gaining the quickest and easiest adjustment of the arch wire to effect correction of tooth inclination and/or rotation. Another advantage is that the practitioner's hand position may be more comfortable in the end-on position of plier 10" than is the case for the two (right and left) sideways positions encountered in the use of plier 10 of FIG. 1 and of plier 10" of FIGS. 9A and 9B. A disadvantage of plier 10" is that the bend formed by die 150, 160 at the one operative end thereof is of one particular hand, and so a second plier 10" is needed to form Z-bends of the opposite hand, so that two pliers 10″ are required to form Z bends to be utilized to provide correction of tooth inclination and/or rotation, i.e. one to provide positive angular correction and another opposite hand plier 10″ to provide negative angular correction.

Orthodontic pliers 10′ and 10″ may be utilized clinically in like manner to that described above in relation to plier 10.

Figure 12A:
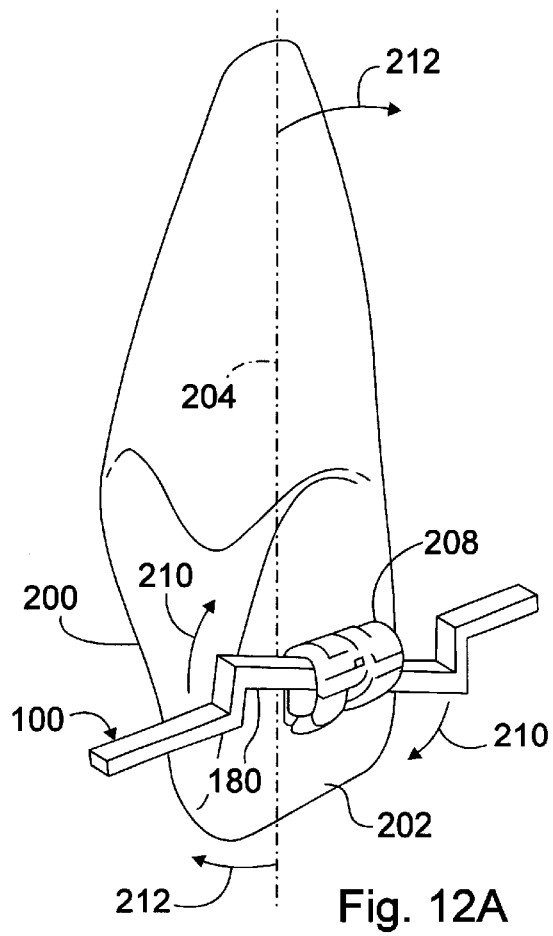
FIGS. 12A and 12B are each illustrations of a Z-bent arch wire in relation to a bracketed tooth.
Figure 12B:
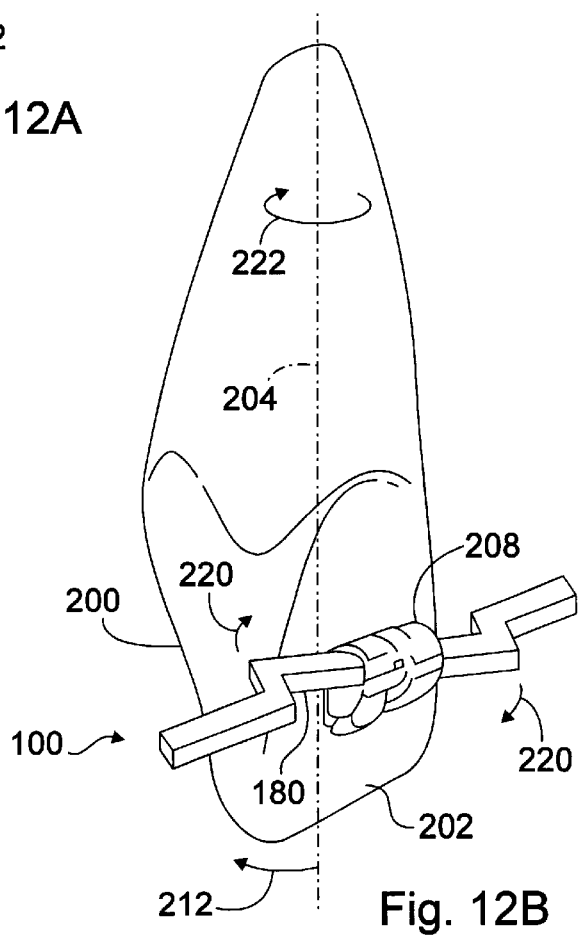

FIGS. 12A and 12B are each illustrations of a portion of an arch wire 100 having a Z-bend 180 or 180′ formed therein, wherein Z-bend 180 or 180′ is installed in an arch wire slot of a bracket 208 that is bonded to a surface 202 of a tooth 200 having a centerline 204, as would be the case in the course of an orthodontic treatment. In FIG. 12A, for example, Z-bend 180 in arch wire 100 is formed in a plane perpendicular to the occlusal plane (which could be referred to as a "horizontal" Z-bend), thus bearing on bracket 208 in a direction to induce forces indicated by arrows 210 on tooth 200, thereby to rotate or angulate the centerline 204 thereof in relation to the occlusal plane in directions indicated by arrows 212. Thus, the horizontal Z-bend 180 is useful for correcting angulation of tooth 200. In analogous fashion, Z-bend 180′ in arch wire 100 in FIG. 12B is formed in a plane parallel to the occlusal plane (which could be referred to as a "vertical" Z-bend), thus bearing on bracket 208 in a direction to induce forces indicated by arrows 220 on tooth 200, thereby to rotate tooth 200 about centerline 204 thereof (i.e. to rotate centerline 204 in relation to the occlusal plane) in the direction indicated by arrow 222. Thus, the vertical Z-bend 180′ is useful for correcting rotation of tooth 200.

While the present invention has been described in terms of the foregoing exemplary embodiments, variations within the scope and spirit of the present invention as defined by the claims following will be apparent to those skilled in the art. For example, the angles $\alpha$, $\beta$ and $\gamma$ of the complementary mating die may be varied consistently with the invention. While an angle $\alpha$ of about 20° is preferred, other angles, e.g., 10°, 30°, 40°, 45° and so forth may be utilized, preferably also adjusting the angles $\beta$ and $\gamma$ to maintain the desired distances Lt, Li and Lo for convenient in situ clinical use. While larger angles of 30°, 40°, 45° may be difficult with standard stainless steel arch wires because central portion of the Z-bend may be too steep and so will not go back into the bracket, or may be distorted in being inserted into the bracket, larger angles would be suitable for nickel-titanium arch wires which, though bent beyond their elastic limit so as to retain the bends of the Z-bend, will straighten any distortion occurring in their being inserted into the brackets as their temperature increases in the patient's mouth. Likewise, instruments having different dimensions Lt, Li, Lo and the like could be utilized for making z-bends of different sizes, as might be advantageous for instruments useful in a child's mouth or in an adult's mouth, or for obtaining different degrees of force for moving a tooth either more or less quickly or to a greater or lesser extent.

In addition, while the instrument described herein is described in terms of a plier, other forms of instruments that can move complementary mating die together and apart so as to form a wire into a Z-bend could be employed in place of a pivoted plier per se. For example, an arrangement having greater mechanical advantage could be employed to obtain greater compressive force on the die 50, 60 or 150, 160 for bending the arch wire. In addition, other instruments such as computer controlled wire forming devices could be employed to form a Z-shaped bend in accordance with the present invention.

Figure 11:
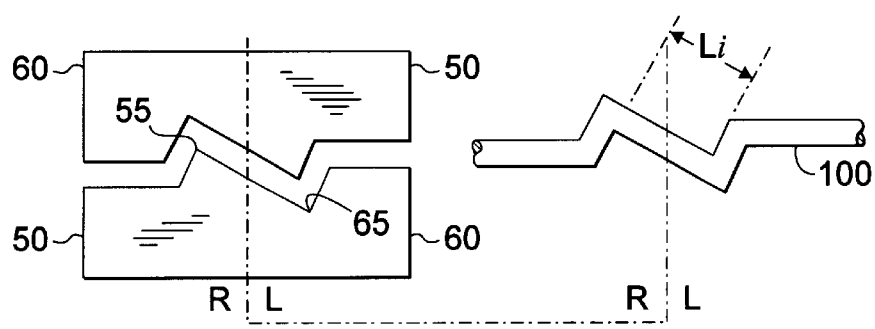
FIG. 11 is a side view of an alternative embodiment of a plier head useful in accordance with the present invention.

Further, the distance between ridge 55 and the exterior end of die 50 along planar surface 56 and the distance between trough 65 and the exterior end of die 60 along planar surface 66 could be shorter than the desired length of the central portion of the "Z", whereby the practitioner would need to judge the length thereof in forming suitable Z-bends, as illustrated in FIG. 11.

Moreover, while the Z-bends in arch wires are generally described in terms of being perpendicular to or parallel to the occlusal plane, they need not be so. Z-bends in other orientations may similarly be employed to correct different degrees of tooth angulation and rotation, as well as combinations thereof.

It is noted that the present invention is suitable for use with any type of bracket or band (whether metal or plastic, or having 2, 3, 4 or 6 or other number of tie wings, or any built in angular or rotational bias angle, or other type, including self-ligating brackets and arch wire tubes on molar bands) and with any type of ligating module (whether an elastic ligature, a plastic o-ring, a thin metal ligature wire or other ligature).

What is claimed is:

1. An orthodontic instrument for bending an arch wire comprising:

a pair of complementary mating die for forming at least two portions of a Z-shaped bend in an arch wire, wherein unbent portions of the arch wire adjacent the Z-shaped bend are substantially co-linear; and a mechanism adapted to move said complementary mating die apart and to move said complementary mating die together;

whereby the arch wire is formed to said Z shape when between said complementary mating die when said die move together.

2. The instrument of claim 1 wherein said mechanism is a plier having respective handle portions and jaw portions pivotally connected, wherein each one of said pair of complementary mating die is attached to a respective one of the jaw portions of said plier.

3. An orthodontic instrument for bending an arch wire comprising:

a pair of complementary mating die for forming at least two portions of a Z-shaped bend in an arch wire. wherein unbent portions of the arch wire adjacent the Z-shaped bend are substantially co-linear, wherein said pair of complementary mating die comprise a male die and a female die, said male die having at least first, second and third planar surfaces, wherein said second planar surface extends upwardly from said first planar surface and intersects said third planar surface to define a ridge line; and a mechanism adapted to move said complementary mating die apart and to move said complementary mating die together.

4. The instrument of claim 3 wherein said third planar surface extends downwardly and intersects the plane of said first planar surface.

5. The instrument of claim 3 wherein said female die has at least first, second and third planar surfaces, wherein said second planar surface thereof extends inwardly from said first planar surface thereof and intersects said third planar surface to define a trough line, said trough line being complementary to the ridge line and mating therewith when said pair of complementary mating die are moved together.

6. The instrument of claim 4 wherein said mechanism has respective jaw portions operably connected, wherein each one of said pair of complementary mating die is attached to a respective one of the jaw portions of said mechanism, and wherein said ridge line and said trough line are substantially transverse to a plane in which said jaw portions of said mechanism lie.

7. The instrument of claim 4 wherein said mechanism has respective jaw portions operably connected, wherein each one of said pair of complementary mating die is attached to a respective one of the jaw portions of said mechanism, and wherein said ridge line and said trough line are substantially parallel to a plane in which said jaw portions of said mechanism lie.

8. The instrument of claim 3 wherein said third planar surface is at an angle between about 10 degrees and 30 degrees with respect to said first planar surface.

9. The instrument of claim 8 wherein said angle is about 20 degrees.

10. The instrument of claim 3 wherein said male die has fourth and fifth planar surfaces, said fifth planar surface being substantially coplanar with said first surface, and said fourth planar surface being substantially parallel to said second planar surface and extending downwardly from said fifth planar surface to intersect said third planar surface at a trough line.

11. The instrument of claim 10 wherein said female die has at least first, second, third, fourth and fifth planar surfaces, wherein said second planar surface thereof extends inwardly from said first planar surface thereof and intersects said third planar surface thereof to define a trough line, said fifth planar surface thereof being substantially coplanar with said first planar surface thereof, and said fourth planar surface thereof being substantially parallel to said second planar surface thereof and extending upwardly from said fifth planar surface thereof to intersect said third planar surface thereof at a ridge line, said trough line and said ridge line of said female die being complementary to the ridge line and trough line of said male die and mating therewith when said pair of complementary mating die are moved together.

12. The instrument of claim 10 wherein said mechanism has respective jaw portions operably connected, wherein each one of said pair of complementary mating die is attached to a respective one of the jaw portions of said mechanism, and wherein said ridge line and said trough line are substantially transverse to a plane in which said jaw portions of said mechanism lie.

13. The instrument of claim 10 wherein said mechanism has respective jaw portions operably connected, wherein each one of said pair of complementary mating die is attached to a respective one of the jaw portions of said mechanism, and wherein said ridge line and said trough line are substantially parallel to a plane in which said jaw portions of said mechanism lie.

14. An orthodontic plier for forming a Z-shaped bend in an arch wire comprising:
   a plier including a pair of handle portions and a pair of jaw portions pivotally connected to allow the jaw portions thereof to move together and apart; and
   a pair of complementary mating die wherein each one of the pair of complementary mating die is attached to a respective one of the jaw portions, said pair of complementary mating die together defining at least two portions of the Z-shaped bend for forming the Z-shaped bend in the arch wire with unbent portions of the arch wire adjacent both ends of the Z-shaped bend being substantially co-linear,
   whereby the arch wire is formed to said Z shape between said complementary mating die when said die move together.

15. An orthodontic plier for forming a Z-shaped bend in an arch wire comprising:
   a plier including a pair of handle portions and a pair of jaw portions pivotally connected to allow the jaw portions thereof to move together and apart; and
   a pair of complementary mating die wherein each one of the pair of complementary mating die is attached to a respective one of the jaw portions, said pair of complementary mating die together defining at least two portions of the Z-shaped bend for forming the Z-shaped bend in the arch wire with unbent portions of the arch wire adjacent both ends of the Z-shaped bend being substantially co-linear,
   wherein said pair of complementary mating die comprise a male die and a female die, said male die having at least first, second and third planar surfaces, wherein said second planar surface extends upwardly from said first planar surface and intersects said third planar surface to define a ridge line.

16. The orthodontic plier of claim 15 wherein said third planar surface extends downwardly and intersects the plane of said first planar surface.

17. The orthodontic plier of claim 16 wherein said female die has at least first, second and third planar surfaces, wherein said second planar surface thereof extends inwardly from said first planar surface thereof and intersects said third planar surface to define a trough line, said trough line being complementary to the ridge line and mating therewith when said pair of complementary mating die are moved together.

18. The orthodontic plier of claim 16 wherein said ridge line and said trough line are substantially transverse to a plane in which said jaw portions of said plier lie.

19. The orthodontic plier of claim 16 wherein said ridge line and said trough line are substantially parallel to a plane in which said jaw portions of said plier lie.

20. The orthodontic plier of claim 15 wherein said third planar surface is at an angle between about 10 degrees and 30 degrees with respect to said first planar surface.

21. The orthodontic plier of claim 20 wherein said angle is about 20 degrees.

22. The orthodontic plier of claim 15 wherein said male die has fourth and fifth planar surfaces, said fifth planar surface being substantially coplanar with said first surface, and said fourth planar surface being substantially parallel to said second planar surface and extending downwardly from said fifth planar surface to intersect said third planar surface at a trough line.

23. The orthodontic plier of claim 22 wherein said female die has at least first, second, third, fourth and fifth planar surfaces, wherein said second planar surface thereof extends inwardly from said first planar surface thereof and intersects said third planar surface thereof to define a trough line, said fifth planar surface thereof being substantially coplanar with said first planar surface thereof, and said fourth planar surface thereof being substantially parallel to said second planar surface thereof and extending upwardly from said fifth planar surface thereof to intersect said third planar surface thereof at a ridge line, said trough line and said ridge line of said female die being complementary to the ridge line and trough line of said male die and mating therewith when said pair of complementary mating die are moved together.

24. The orthodontic plier of claim 22 wherein said ridge line and said trough line are substantially transverse to a plane in which said jaw portions of said plier lie.

25. The orthodontic plier of claim 22 wherein said ridge line and said trough line are substantially parallel to a plane in which said jaw portions of said plier lie.

26. A method of adjusting an arch wire of an orthodontic appliance comprising:

identifying a tooth to be angulated and/or rotated;

releasing the arch wire from a bracket on the identified tooth and from brackets on at least one tooth distal and one tooth mesial therefrom;

forming a Z-shaped bend in the arch wire using a Z-bend forming instrument, the Z-shaped bend having a longer diagonal portion between two shorter portions;

placing a longer diagonal portion of the Z-shaped bend into the bracket of the identified tooth; and securing the arch wire in the brackets on the identified tooth and on the at least one tooth distal and one tooth mesial therefrom.

27. The method of claim 26 wherein said releasing the arch wire includes removing ligating modules from the brackets on the identified tooth and on the at least one tooth distal and one tooth mesial therefrom.

28. The method of claim 26 wherein said forming a Z-shaped bend includes placing the arch wire between a pair of complementary mating die defining the Z-shaped bend and moving the pair of complementary mating die together to form the arch wire.

29. The method of claim 26 wherein said forming a Z-shaped bend includes:

placing the arch wire between a pair of complementary mating die defining at least one of the parallel shorter portions of the Z-shaped bend and the longer diagonal portion adjacent thereto, and moving the pair of complementary mating die together a first time to form the one of the parallel shorter portions and the longer diagonal portion of the Z-shaped bend in the arch wire;

reversing the position of the pair of complementary mating die with respect to the arch wire; and placing the arch wire between the pair of complementary mating die with the portion thereof defining the longer diagonal portion over the longer diagonal portion already formed in the arch wire and moving the pair of complementary mating die together a second time to form the other one of the shorter parallel portions of the Z-shaped bend adjacent the longer diagonal portion thereof, thereby to complete the Z-shaped bend formed in the arch wire.

30. The method of claim 26 wherein the two shorter portions of the Z-shaped bend are substantially parallel to each other.

31. The method of claim 26 wherein said securing the arch wire includes placing the arch wire into the brackets on the identified tooth and on the at least one tooth distal and one tooth mesial therefrom, and installing ligating modules on the brackets.

32. The method of claim 26 wherein said forming a Z-shaped bend includes forming the Z-shaped bend substantially in a plane parallel to the occlusal plane for rotating the identified tooth.

33. The method of claim 26 wherein said forming a Z-shaped bend includes forming the Z-shaped bend substantially in a plane perpendicular to the occlusal plane for angulating the identified tooth.

34. The method of claim 26 wherein said forming a Z-shaped bend includes forming the Z-shaped bend substantially in a plane at an angle between parallel to the occlusal plane and perpendicular to the occlusal plane for angulating and rotating the identified tooth.

35. A method of adjusting an orthodontic appliance comprising:

identifying a tooth to be angulated and/or rotated;

obtaining an arch wire and identifying thereon the location of a bracket for the identified tooth;

forming a Z-shaped bend at the identified location of the arch wire, the Z-shaped bend having at the identified location a longer diagonal portion between two shorter portions;

placing the longer diagonal portion of the Z-shaped bend into the bracket of the identified tooth; and securing the arch wire on the identified tooth and on at least one tooth distal and one tooth mesial therefrom.

36. The method of claim 35 wherein the two shorter portions of the Z-shaped bend are substantially parallel to each other.

37. The method of claim 35 wherein said forming a Z-shaped bend includes forming the Z-shaped bend substantially in a plane parallel to the occlusal plane for rotating the identified tooth.

38. The method of claim 35 wherein said forming a Z-shaped bend includes forming the Z-shaped bend substantially in a plane perpendicular to the occlusal plane for angulating the identified tooth.

39. The method of claim 35 wherein said forming a Z-shaped bend includes forming the Z-shaped bend substantially in a plane at an angle between parallel to the occlusal plane and perpendicular to the occlusal plane for rotating and angulating the identified tooth.

40. The method of claim 35 wherein said securing the arch wire includes placing the arch wire into brackets on the identified tooth and on at least one tooth distal and one tooth mesial therefrom, and installing ligating modules on the brackets.

41. The method of claim 35 wherein said forming a Z-shaped bend includes placing the arch wire between a pair of complementary mating die defining the Z-shaped bend and moving the pair of complementary mating die together to form the arch wire.

42. An orthodontic instrument for bending an arch wire comprising:

a pair of complementary mating die for forming at least two bends defining at least two portions of a Z-shaped bend in an arch wire, wherein unbent portions of the arch wire adjacent the Z-shaped bend are substantially co-linear; and a mechanism adapted to move said complementary mating die apart and to move said complementary mating die together;

whereby the arch wire is formed to said Z shape when between said complementary mating die when said die move together.

43. An orthodontic plier for forming a Z-shaped bend in an arch wire comprising:

a plier including a pair of handle portions and a pair of jaw portions pivotally connected to allow the jaw portions thereof to move together and apart; and a pair of complementary mating die wherein each one of the pair of complementary mating die is attached to a respective one of the jaw portions, wherein said pair of complementary mating die together are for forming at least two bends in the arch wire defining at least two portions of the Z-shaped bend in the arch wire with unbent portions of the arch wire adjacent both ends of the Z-shaped bend being substantially co-linear, whereby the arch wire is formed to said Z shape between said complementary mating die when said die move together.

* * * * *